United States Patent [19]

Worthington et al.

[11] 4,277,469

[45] Jul. 7, 1981

[54] HETEROCYCLIC TRIAZOLE COMPOUNDS, PROCESSES FOR THEIR PREPARATION, PESTICIDAL COMPOSITIONS CONTAINING THEM, AND METHODS OF COMBATING PESTS

[75] Inventors: Paul A. Worthington, Maidenhead; William G. Rathmell; Anthony M. Skidmore, both of Wokingham, all of England

[73] Assignee: Imperial Chemical Industries Limited, London, England

[21] Appl. No.: 58,445

[22] Filed: Jul. 18, 1979

[30] Foreign Application Priority Data

Jul. 27, 1978 [GB] United Kingdom ............... 31318/78

[51] Int. Cl.$^3$ .................... A01N 43/64; C07D 233/58; C07D 249/08; C07D 233/60
[52] U.S. Cl. .................... 424/245; 424/269; 424/273 R; 542/429; 542/440; 542/468; 548/101; 548/262; 548/341
[58] Field of Search .................. 548/101, 262, 341; 424/245, 269, 273 R; 71/92; 542/429, 440, 468

[56] References Cited

U.S. PATENT DOCUMENTS

| 4,086,351 | 4/1978 | Balasubramanyan et al. | 548/262 |
| 4,130,409 | 12/1978 | Shephard et al. | 424/269 |

FOREIGN PATENT DOCUMENTS

| 2734426 | 2/1978 | Fed. Rep. of Germany | 424/269 |
| 2802496 | 7/1978 | Fed. Rep. of Germany | 424/269 |
| 2819879 | 11/1978 | Fed. Rep. of Germany | 548/341 |

Primary Examiner—Alton D. Rollins
Attorney, Agent, or Firm—Cushman, Darby & Cushman

[57] ABSTRACT

Compounds of formula:

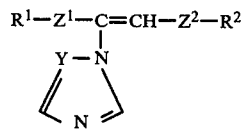

and isomers thereof, wherein $R^1$ and $R^2$ are alkyl, cycloalkyl or phenyl, Y is =N— or =CH— and one of $Z^1$ and $Z^2$ is carbonyl (or a functional derivative thereof) and the other is CHOH, and esters, ethers, salts and metal complexes thereof, have fungicidal, plant growth regulating and herbicidal activity.

8 Claims, No Drawings

HETEROCYCLIC TRIAZOLE COMPOUNDS, PROCESSES FOR THEIR PREPARATION, PESTICIDAL COMPOSITIONS CONTAINING THEM, AND METHODS OF COMBATING PESTS

This invention relates to imidazole and triazole compounds useful as fungicides, herbicides and plant growth regulators; to a process for preparing them; to compositions containing them; and to methods of using them to combat fungal infections in plants and to control the growth of vegetation.

The invention provides compounds having the general formula (I)

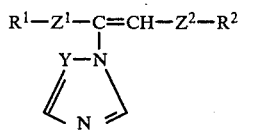

wherein each of $R^1$ and $R^2$, which may be the same or different, is unsubstituted or alkyl-substituted cycloalkyl, unsubstituted or halo-substituted alkyl or unsubstituted or substituted phenyl, Y is =N— or =CH— and one of $Z^1$ and $Z_2$ is C=O or a functional derivative thereof (e.g. an imine, oxime, ketal, hydrazone or semicarbazone) and the other is —CH(OH)—; and esters, ethers, acid addition salts and metal complexes thereof; and any isomer of the foregoing.

The compounds of the invention contain chiral centres. The compounds are generally obtained in the form of racemic mixtures. However, these and other mixtures can be separated into the individual isomers by methods known in the art e.g. chromatography. In many cases, the compounds can be prepared stereospecifically in the form of a single diastereoisomer.

The compounds also form geometrical isomers; mixtures of these isomers can be separated by methods known in the art.

The alkyl groups, which can be straight or branched chain, preferably have 1 to 5 carbon atoms; examples are methyl, ethyl, propyl (n- or i-propyl) and butyl (n-, i- or t-butyl).

Suitable substituents for the phenyl group are halogen, $C_{1-4}$ alkyl [e.g. methyl, ethyl, propyl (n- or i-propyl) and butyl (n-, i- or t-butyl)], halo($C_{1-4}$ alkyl) (e.g. chloro- or bromo- methyl), hydroxy ($C_{1-4}$ alkyl) (e.g. hydroxymethyl), phenyl, halophenyl (e.g. chlorophenyl), cycloalkyl, nitro, cyano, $C_{1-4}$ alkoxy (e.g. methoxy, ethoxy, propoxy or butoxy), $C_{2-4}$ alkenyloxy (e.g. allyloxy), ($C_{1-4}$ alkylene)dioxy (e.g. methylenedioxy), ($C_{1-4}$alkoxy) ($C_{1-4}$ alkyl) [e.g. methoxy- or ethoxy-methyl or 2-methoxy- or ethoxy-ethyl], mercapto, ($C_{1-4}$ alkyl) thio [e.g. methyl- or ethyl-thio], ($C_{1-4}$ alkyl) sulphonyl [e.g. methyl- or ethyl-sulphonyl], ($C_{1-4}$ haloalkyl)sulphonyl [e.g. trifluoromethylsulphonyl], phenylsulphonyl, unsubstituted or mono- or di- ($C_{1-4}$ alkyl) substituted sulphamoyl or carbamoyl, 1-pyrrolidinylsulphonyl, carboxy, ($C_{1-4}$ alkoxy)carbonyl [e.g. methoxy- or ethoxy-carbonyl], hydroxy, $C_{1-6}$ alkanoyloxy, benzoyloxy, carboxy ($C_{1-4}$ alkyl)oxy (e.g. carboxymethoxy or 1-carboxyethoxy), unsubstituted or mono- or di- ($C_{1-4}$ alkyl) substituted amino, ($C_{1-6}$ alkanoyl)amino, N-($C_{1-4}$ alkyl)-N-($C_{1-6}$ alkanoyl)amino, formylamino, N-($C_{1-4}$ alkyl) formylamino, phenylethyl, methylenedioxyphenyl, phenoxy or benzyloxy. A suitable alkanoyl is acetyl or propionyl. The phenyl group can have more than one substituent; examples of polysubstituted groups are those substituted with up to the maximum possible number (especially 1, 2 or 3) of for example halogen (particularly chlorine) atoms and/or nitro, methyl or methoxy groups.

Examples of suitable phenyl groups are phenyl itself, chlorophenyl (for example o-, m- or p-chlorophenyl), dichlorophenyl (e.g. 3,4-, 2,4-, 3,5- or 2,6-dichlorophenyl), trichlorophenyl (e.g. 2,3,6- or 2,4,5-trichlorophenyl), tetrachlorophenyl, pentachlorophenyl, bromophenyl (e.g. o-, m- or p-bromophenyl), dibromophenyl (e.g. 2,4-dibromophenyl), fluorophenyl (e.g. o-, m- or p-fluorophenyl), difluorophenyl (e.g. 2,4- or 3,4-difluorophenyl), pentafluorophenyl, iodophenyl (e.g. o-iodophenyl), aminophenyl (e.g. p-aminophenyl), methylphenyl (e.g. o-, m- or p-methylphenyl), dimethylphenyl (e.g. 2,6-, 2,5- and 3,4-dimethylphenyl), ethylphenyl (e.g. p-ethylphenyl), propylphenyl (e.g. p-i-propylphenyl), butylphenyl (e.g. p-t-butylphenyl), cyanophenyl (e.g. o-, m- or p-cyanophenyl), nitrophenyl (e.g. o-, m- or p-nitrophenyl), dinitrophenyl (e.g. 2,4-dinitrophenyl), cyanochlorophenyl (e.g. 3-cyano-4-chlorophenyl or 4-cyano-3-chlorophenyl), methylsulphonylphenyl (e.g. p-methylsulphonylphenyl), sulphamoylphenyl (e.g. p-sulphamoylphenyl), N,N-dimethylsulphamoylphenyl [e.g. p-(N,N-dimethylsulphamoyl)phenyl], pyrrolidin-1-ylsulphonylphenyl (e.g. p-pyrrolidin-1-ylsulphonylphenyl), trifluoromethylsulphonylphenyl (e.g. p-trifluoromethylsulphonylphenyl), methylthiophenyl (e.g. p-methylthiophenyl), (chloromethyl)phenyl [e.g. o-, m- or p-(chloromethyl)phenyl], (bromomethyl)phenyl [e.g. o-, m- or p-(bromomethyl)phenyl], (hydroxymethyl)phenyl [e.g. o-, m- or p-(hydroxymethyl)phenyl], (methoxymethyl)phenyl [e.g. o-, m- or p-(methoxymethyl)phenyl], carboxyphenyl (e.g. o-, m- or p-carboxyphenyl), methoxycarbonylphenyl (e.g. o-, m- or p-methoxycarbonylphenyl), N,N-dimethylcarbamoylphenyl [e.g. o-, m- or p-(N,N-dimethylcarbamoyl)phenyl], N,N-dimethylaminophenyl [e.g. o-, m- or p-(N,N-dimethylamino)phenyl], hydroxyphenyl (e.g. o-, m- or p-hydroxyphenyl), acetoxyphenyl (e.g. o-, m- or p-acetoxyphenyl), benzoyloxyphenyl (e.g. o-, m- or p-benzoyloxyphenyl), (trifluoromethyl)phenyl [e.g. o-, m- or p-(trifluoromethyl)phenyl], methoxyphenyl (e.g. o-, m- or p-methoxyphenyl), dimethoxyphenyl (e.g. 2,4-, 3,4- or 3,5-dimethoxyphenyl), ethoxyphenyl (e.g. o-, m- or p-ethoxyphenyl), propoxyphenyl (e.g. p-i-propoxyphenyl or p-n-propoxyphenyl), butoxyphenyl (e.g. o-, m- or p-i-butoxyphenyl), allyloxyphenyl (e.g. o-, m- or p-allyloxyphenyl), carboxymethoxyphenyl (e.g. o-, m- or p-carboxymethoxyphenyl), 1-carboxyethylphenyl [e.g. o-, m- or p-(1-carboxyethyl)phenyl], chloronitrophenyl (e.g. 3-nitro-4-chlorophenyl), fluoronitrophenyl (e.g. 2-nitro-4-fluorophenyl), chlorofluorophenyl (e.g. 2-fluoro-4-chlorophenyl, 2-chloro-6-fluorophenyl or 2-chloro-4-fluorophenyl), fluorobromophenyl (e.g. 2-fluoro-4-bromophenyl), methylenedioxychlorophenyl (e.g. 2-chloro-4,5-methylenedioxyphenyl), methoxychlorophenyl (e.g. 3-chloro-4-methoxyphenyl), methoxybromophenyl (e.g. 2-methoxy-5-bromophenyl or 3-bromo-4-methoxyphenyl), methoxynitrophenyl (e.g. 2-methoxy-5-nitrophenyl or 4-methoxy-3-nitrophenyl), ethoxynitrophenyl (e.g. 4-ethoxy-3-nitrophenyl), ethoxychlorophenyl (e.g. 4-ethoxy-3-chlorophenyl), ethoxybromophenyl (e.g. 4-ethoxy-3-bromo phenyl), benzyloxyphenyl (e.g. p-benzyloxyphenyl), phenylphenyl (e.g. p-phenylphenyl) or methylenedioxyphenylphenyl (e.g. 3,4-methylenedioxyphenylphenyl).

The cycloalkyl group suitably has 3 to 6 carbon atoms: preferably it is cyclopropyl, cyclopentyl, cyclohexyl or methylcyclohexyl.

Preferably the haloalkyl group contains 1 to 3 halogen atoms; examples are 2-chloroethyl, trifluoromethyl or trichloromethyl.

The halogen can be fluorine, chlorine, bromine or iodine.

Suitable salts are salts with inorganic or organic acids, e.g. hydrochloric, nitric, sulphuric, toluene-sulphonic, acetic or oxalic acid. The esters are suitably alkanoates (e.g. acetates) and the ethers are suitably alkyl (e.g. methyl or ethyl), aryl (e.g. phenyl) or aralkyl (e.g. benzyl) ethers.

The metal complex is suitably one including copper, zinc, manganese or iron. It preferably has the general formula:

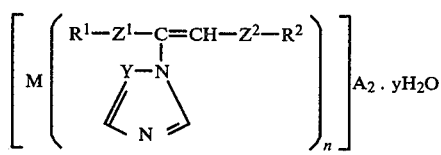

wherein Y, $R^1$, $R^2$, $Z^1$ and $Z^2$ are as defined above, M is a metal, A is an anion (e.g. a chloride, bromide, iodide, nitrate, sulphate or phosphate anion), n is 2 or 4 and y is 0 or an interger of 1 to 12.

Examples of the triazole compounds of general formula (I) are given in Table I.

TABLE I

| COMPOUND NO | $R^1$ | $R^2$ | $Z^1$ | $Z^2$ | MELTING POINT (°C.) |
|---|---|---|---|---|---|
| 1 | p-Cl—$C_6H_4$ | —$C(CH_3)_3$ | CHOH | C=O | 156 –160° |
| 2 | —$C(CH_3)_3$ | —$C(CH_3)_3$ | CHOH | C=O | 142 –145° |
| 3 | —$C(CH_3)_2$ | —$C(CH_3)_3$ | CHOH | C=O | 104 –107° |
| 4 | p-F—$C_6H_4$ | —$C(CH_3)_3$ | CHOH | C=O | 141 –145° |

The compounds (and the salts and complexes) of the invention may be made by selectively reducing a diketone of general formula (II):

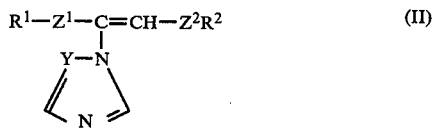

wherein Y, $R^1$ and $R^2$ are as defined above, and the groups $Z^1$ and $Z^2$ are C=O, or a salt or metal complex thereof, with for example a metal hydride reducing agent (e.g. lithium aluminium hydride, sodium borohydride or aluminium isopropoxide) in an inert polar solvent (e.g. water or ethanol).

The starting materials for the above process may be made by reacting imidazole or 1,2,4-triazole or a salt thereof with the appropriate dihalo-δ-diketone of general formula (III):

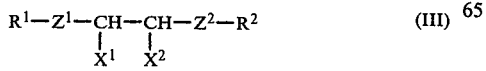

wherein $R^1$, $R^2$, $Z^1$ and $Z^2$ are as defined above for the compound of general formula (II), and each of the groups $X^1$ and $X^2$, which may be the same or different, is halogen (e.g. chlorine or bromine). This process is suitably carried out by heating the reactants together in a suitable solvent (such as acetonitrile, tetrahydrofuran or dimethylformamide); preferably it is performed by reacting the sodium salt of triazole or imidazole with a dibromo-δ-diketone in for example boiling dimethylformamide. The product can be isolated by pouring the reaction mixture into water and recrystallising the product from a convenient solvent.

The dihalo-δ-diketone starting material may be made by halogenation (e.g. bromination) of a compound of general formula (IV):

$$R^1-Z^1-CH=CH-Z^2-R^2 \qquad (IV)$$

wherein $R^1$, $R^2$, $Z^1$ and $Z^2$ are as defined above for the compound of general formula (II). Suitable brominating agents are bromine itself, N-bromosuccinimide and pyridinium hydrobromide perbromide.

The compounds of general formula (IV) may be made by methods set out in the literature.

The compounds of general formula (II) may also be made by reacting a compound of general formula (V):

where Y and $R^1$ are as defined above and $Z^1$ is C=O, with a compound of general formula (VI):

$$OHC-Z^2-R^2 \qquad (VI)$$

where $R^2$ is as defined above and $Z^2$ is C=O, in the presence of a base (e.g. sodium methoxide or N-methylaniline magnesium bromide) to give a compound of general formula (VII):

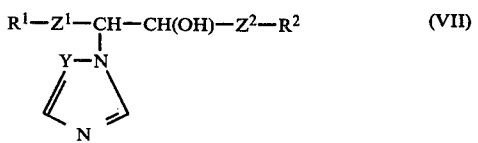

wherein Y, $R^1$ and $R^2$ are as defined above and $Z^1$ and $Z^2$ are C=O. The compound of general formula (VII) can be dehydrated under standard conditions to give the compound of general formula (II). The dehydration is suitably achieved by using p-toluene sulphonyl chloride in pyridine.

The compounds of general formula (V) and (VI) may be made by methods set out in the literature.

The salts, metal complexes, ethers and esters of the compounds of general formula (I) can be prepared from the latter in known manner. For example, the complexes can be made by reacting the uncomplexed compound with a metal salt in a suitable solvent. The substituent on the phenyl group in the compound of general formula (I) can often be changed by methods known in the art. For example, a compound wherein for example $R^1$ is phenyl substituted with carboxy can be prepared from the corresponding compound wherein $R^1$ is phenyl substituted with alkoxycarbonyl, and vice-versa.

The compounds are active fungicides, particularly against the diseases:

Pyricularia oryzae on rice

Puccinia recondita, Puccinia striiformis and other rusts on wheat, Puccinia hordei, Puccinia striiformis and other rusts on barley, and rusts on other hosts, e.g. coffee, apples, vegetables and ornamental plants Erysiphe graminis (powdery mildew) on barley and wheat and other powdery mildews on various hosts such as Helminthosporium spp. on cereals, Sphaerotheca fuliginea on cucurbits (e.g. cucumber), Podosphaera leucotricha on apples and Uncinula necator on vines Cercospora arachidicola on peanuts and other Cercospora species on for example sugar beet, bananas and soya beans Botrytis cinerea (grey mould) on tomatoes, strawberries, vines and other hosts Venturia inaequalis (scab) on apples Some of the compounds have also shown a broad range of activities against fungi in vitro. They have activity against various post-harvest diseases on fruit (e.g. Penicillium digatatum and italicum on oranges and Gloeosporium musarum on bananas). Further some of the compounds are active as seed dressings against: Fusarium spp., Septoria spp., Tilletia spp. (i.e. bunt, a seed borne disease of wheat), Ustilago spp., Helminthosporium spp. on cereals, Rhizoctonia solani on cotton and Corticium sasakii on rice.

The compounds of the invention and functional derivatives, esters, ethers, salts, metal complexes and isomers thereof may be effectively used for application to the foliage of plants by spraying and other techniques. They also show acropetal systemic movement in plants, that is they have a capacity to move from root or seed through stem and shoot to leaves and other aerial parts. The compounds of the invention, and functional derivatives, esters, ethers, salts, metal complexes and isomers thereof are therefore useful as seed dressings or for soil (in furrow) application.

They also variously display plant growth regulating, gametocidal and herbicidal activity. For example Compound No 2 of Table I possesses gametocidal activity and Compound No 4 of Table I displays herbicidal activity. All four compounds of Table I variously display growth regulating effects upon plants.

The compounds may be used as such for fungicidal, plant growth regulating and herbicidal purposes but are more conveniently formulated into compositions for such usage. The invention therefore further provides a composition for the foregoing uses comprising as an active ingredient, a compound of general formula (I), or a functional derivative, ester, ether, acid addition salt, or metal complex of such a compound; or any isomer thereof, as hereinbefore defined, and a carrier or diluent.

The invention also provides a method of combating fungal diseases in, or regulating the growth of, plants, which method comprises applying to a plant, to seed of a plant, or to the locus of a plant or seed, a compound or a functional derivative, ester, ether, acid addition salt or metal complex of such a compound; or any isomer thereof.

The compounds, salts, complexes, ethers and esters etc., can be applied in a number of ways, for example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, keiselguhr, dolomite, calcium carbonate, talc, powdered magnesia, Fuller's earth, gypsum, Hewitt's earth, diatomaceous earth and China clay. Such granules can be performed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound, are preferred. Such granules suitably contain up to 25% by weight of the compound. The invention therefore also provides a fertiliser composition comprising the compound of general formula (I) or a salt, metal complex, ether or ester; or any isomer of any of the foregoing.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s). These agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butyl-naphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient(s). These concentrates suitably contain organic acids (e.g. alkaryl or aryl sulphonic acids such as xylenesulphonic acid or dodecylbenzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, e.g. compounds having similar or complementary fungicidal or compounds having herbicidal, plant growth regulating or insecticidal activity.

The other fungicidal compound can be for example one which is capable of combating ear diseases of cereals (e.g. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compounds are imazalil, benomyl, carbendazim (BCM), thiophanate-methyl, captafol, captan, sulphur, dithiocarbamates, carbathiins, copper oxychloride, triforine, dodemorph, tridemorph, dithianon, pyrazophos, binapacryl, quinomethionate, panoctine, furalaxyl, aluminium trio(ethyl phosphonate), DPX3217, ethirimol, dimethirimol, bupirimate, chlorothalonil and metaxanine.

The compounds of general formula (I) can be mixed with soil, peat or other rooting media for the protection of plants against seed-borne, soil-borne or foliar fungal diseases.

The following Examples illustrate the invention; the temperatures are given in degrees Centigrade (°), and percentages are by weight.

EXAMPLE 1

4-(1,2,4-Triazol-1-yl)-2,2,7,7-tetramethyl-oct-4-en-3-ol-6-one

Stage 1. A stirred solution of 2,2,7,7-tetramethyloct-4-en-3, 6-dione (0.1 mol; m.p. 107°–9°; prepared according to the method of Ramasseul and Rassat, Bull. Soc. Chim. Fr., 1963, 2214–2217) in diethyl ether (200 ml) was treated dropwise with bromine (0.1 mol) at room temperature. After the bromine colour had been discharged, the ether was removed in vacuo to give a white crystalline solid. Recrystallisation from ethanol gave 2,2,7,7-tetramethyl-4,5-dibromo-octan-3,6-dione (yield 90%), m.p. 110°–111°.

Stage 2. Sodium hydride (100%, 0.06 mol) was added to a suspension of triazole (0.06 mol) in dimethylformamide (100 ml) and the solution stirred at 20° until effervescence ceased. The product (0.03 mol) of Stage 1 was added portionwise at 20° to the stirred solution. After refluxing for 2 hours, the solution was cooled and poured into water to give a crystalline solid. Recrystallisation from petroleum ether (60°–80°) gave 4-(1,2,4-triazol-1-yl)-2,2,7,7-tetramethyl-oct-4-en-3,6-dione as a white crystalline solid, m.p. 107°–8°.

Stage 3. The product (1.8 g) of Stage 2 was dissolved in dry methanol (20 ml) and sodium hydride (100 mgs) added portionwise to this solution at 0°. After stirring at 0° for 1 hour the methanol was removed in vacuo and the residue washed several times with water to give a white crystalline solid which recrystallised from petroleum ether/ethanol to give the title compound, m.p. 142°–5°.

Compound No 4 of Table I was prepared similarly using the appropriate starting substances.

EXAMPLE 2

2-(1,2,4-Triazol-1-yl)-1-p-chlorophenyl-5,5-dimethyl-hex-2-en-1-ol-4-one

Stage 1. Freshly distilled 4-butyl glyoxal (3.2 g; 0.03 mol) in tetrahydrofuran (THF; 5 ml) was added dropwise to a solution of N-methylaniline magnesium bromide (0.03 mol) in tetrahydrofuran (40 ml) at 0° to give a deep red solution. 1-(p-Chlorophenacyl) triazole (5.5 g; 0.025 mol) was added portionwise at 0° to give a white precipitate. After stirring for 15 minutes at 0°, the white solid was filtered off to give 2-(1,2,4-triazol-1-yl)-

1-p-chlorophenyl-5,5-dimethyl-hexan-1,4-dione-3-ol (4.1 g; yield 49%), m.p. 174°–5°.

Stage 2. The product (4.9 g, 0.015 mol) of Stage 1 and p-toluenesulphonyl chloride (3.0 g, 0.06 mol) were mixed together in pyridine (50 ml) at 20°. After standing at room temperature for 48 hours, the solution was poured into crushed ice (50 ml)/concentrated hydrochloric acid (50 ml). The mixture was extracted with diethyl ether (100 ml), and the extract washed with water (3×100 ml) and dried over anhydrous sodium sulphate. Removal of the ether gave a brown gum which was further purified by column chromatography (silica gel eluted with diethyl ether) to give 2-(1,2,4-triazol-1-yl)-1-p-chlorophenyl-5,5-dimethyl-hex-2-en-1,4-dione as a gum (2.8 g; yield 60%).

Stage 3. The product (6.4 g, 0.02 mol) of Stage 2 was dissolved in methanol (100 ml) and to this solution was added sodium borohydride (0.2 g, 0.005 mol) at 0°. After stirring at room temperature for 15 hours the methanol was removed in vacuo. The residue was washed with water and neutralised with dilute hydrochloric acid. Recrystallisation of the solid from petroleum ether/ethanol gave the title compound as white needles, m.p. 156°–160°.

Compound No 3 of Table I was similarly prepared using the appropriate starting substances.

EXAMPLE 3

An emulsifiable concentrate was made up by mixing the ingredients, and stirring the mixture until all the constituents were dissolved.

| | |
|---|---|
| Compound No 1 of Table I | 10% |
| Ethylene dichloride | 40% |
| Calcium dodecylbenzenesulphate | 5% |
| "Lubrol" L | 10% |
| "Aromasol" H | 35% |

EXAMPLE 4

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44-100, to obtain the desired size of grains.

| | |
|---|---|
| Compound No 2 of Table I | 50% |
| "Dispersol" T | 25% |
| "Lubrol" APN 5 | 1.5% |
| Sodium acetate | 23.5% |

EXAMPLE 5

The ingredients were all ground together to produce a powder formulation readily dispersible in liquids.

| | |
|---|---|
| Compound No 3 of Table I | 45% |
| "Dispersol" T | 5% |
| "Lissapol" NX | 0.5% |
| "Cellofas" B600 | 2% |
| Sodium acetate | 47.5% |

EXAMPLE 6

The active ingredient was dissolved in a solvent and the resultant liquid was sprayed on to the granules of China clay. The solvent was then allowed to evaporate to produce a granular composition.

| | |
|---|---|
| Compound No 4 of Table I | 5% |
| China clay granules | 95% |

EXAMPLE 7

A composition suitable for use as a seed dressing was prepared by mixing the three ingredients.

| | |
|---|---|
| Compound No 1 of Table I | 50% |
| Mineral oil | 2% |
| China clay | 48% |

EXAMPLE 8

A dusting powder was prepared by mixing the active ingredient with talc.

| | |
|---|---|
| Compound No 2 of Table I | 5% |
| Talc | 95% |

EXAMPLE 9

A Col formulation was prepared by ball-milling the constituents set out below and then forming an aqueous suspension of the ground mixture with water.

| | |
|---|---|
| Compound No 3 of Table I | 40% |
| "Dispersol" T | 10% |
| "Lubrol" APN5 | 1% |
| Water | |

EXAMPLE 10

A dispersible powder formulation was made by mixing together the ingredients set out below and then grinding the mixture until all were thoroughly mixed.

| | |
|---|---|
| Compound No 4 of Table I | 25% |
| "Aerosol" OT/B | 2% |
| "Dispersol" A.C. | 5% |
| China clay | 28% |
| Silica | 40% |

EXAMPLE 11

This Example illustrates the preparation of a dispersible powder formulation. The ingredients were mixed and the mixture then ground in a comminution mill.

| | |
|---|---|
| Compound No 1 of Table I | 25% |
| "Perminal" BX | 1% |
| "Dispersol" T | 5% |
| Polyvinylpyrrolidone | 10% |
| Silica | 25% |
| China clay | 34% |

EXAMPLE 12

The ingredients set out below were formulated into a dispersible powder by mixing then grinding the ingredients.

| | |
|---|---|
| Compound No 2 of Table I | 25% |
| "Aerosol" OT/B | 2% |
| "Dispersol" A | 5% |
| China clay | 68% |

In Examples 3 to 12 the porportions of the ingredients given are by weight.

There now follows an explanation of the compositions or substances represented by the various Trade Marks and Trade Names mentioned above.

TABLE II

| COMPOUND NO | PUCCINIA RECONDITA (wheat) | BOTRYTIS CINEREA (tomato) | ERYSIPHE GRAMINIS (barley) | CERCOSPORA ARACHIDICOLA (peanut) | VENTURIA INAEQUALIS (apple) |
|---|---|---|---|---|---|
| 1 | 3 | 3 | 4 | — | 1 |
| 2 | 4 | 3 | 4 | — | 3 |
| 3 | 0 | 0 | 4 | 2 | 0 |
| 4 | 3 | 1 | 4 | 2 | 1 |

"-" means not tested

| | |
|---|---|
| LUBROL L: | a condensate of nonyl phenol (1 mole) with ethylene oxide (13 moles) |
| AROMASOL H: | a solvent mixture of alkyl-benzenes |
| DISPERSOL T & AC: | a mixture of sodium sulphate and a condensate of formaldehyde with sodium naphthalene sulphonate |
| LUBROL APN5: | a condensate of nonyl phenol (1 mole) with naphthalene oxide (5.5 moles) |
| CELLOFAS B600: | a sodium carboxymethyl cellulose thickener |
| LISSAPOL NX: | a condensate of nonyl phenol (1 mole) with ethylene oxide (8 moles) |
| AEROSOL OT/B: | dioctyl sodium sulphosuccinate |
| PERMINAL BX: | a sodium alkyl naphthalene sulphonate |

EXAMPLE 13

The compounds were tested against a variety of foliar fungal diseases of plants. The techniques employed were as follows:

The plants were grown in John Innes Potting Compost (No. 1 or 2) in 4 cm diameter mini-pots. A layer of fine sand was placed at the bottom of the pots containing the dicotyledonous plants to facilitate the uptake of test compound by the roots. The test compounds were formulated either by bead-milling with aqueous 'Dispersol' T or as a solution in acetone or acetone/ethanol which was diluted to the required concentration immediately before use. For the foliage diseases, suspensions (100 ppm active ingredient) were sprayed on to the foliage and applied to the roots of the same plant via the soil. Exceptions were the tests on *Botrytis cinerea* and *Venturia inaequalis*, in which the compound was sprayed on to the foliage only. Sprays were applied to maximum retention and root drenches to a final concentration equivalent to approximately 40 ppm a.i./dry soil. Tween 20, to give a final concentration of 0.05% was added when the sprays were applied to cereals.

For most of the tests the compound was applied to the soil (roots) and to the foliage (by spraying) one or two days before the plant was inoculated with the diseases. An exception was the test on *Erysiphe graminis* in which the plants were inoculated 24 hours before treatment. After inoculation, the plants were put into an appropriate environment to allow infection to take place and then incubated until the disease was ready for assessment. The period between inoculation and assessment varied from four to fourteen days according to the disease and environment.

The disease control was recorded by the following grading:
4=No disease
3=0–5%
2=6–25%
1=26–60%
0=>60%

The results are shown in Table II.

We claim:

1. A triazole compound having the formula

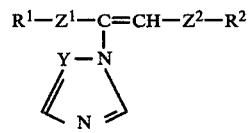

wherein each of $R^1$ and $R^2$, which may be the same or different, is straight or branched chain alkyl having from 1 to 5 carbon atoms optionally substituted with 1 to 3 halogen atoms; cycloalkyl having from 3 to 6 carbon atoms; or phenyl optionally substituted with one or more halogen atoms or $C_{1-4}$ alkyl, halo $C_{1-4}$ alkyl, hydroxy $C_{1-4}$ alkyl, phenyl, halophenyl, nitro, cyano or $C_{1-4}$ alkoxy, Y is =N— and one of $Z^1$ and $Z^2$ is —C=O and the other is —CH(OH)—; and the alkanoate esters, alkyl, aryl or aralkyl ethers, acid addition salts and copper, zinc, manganese or iron complexes thereof.

2. A compound according to claim 1 wherein $Z^1$ is —CHOH, $Z^2$ is C=O, $R^1$ is p-Cl-$C_6H_4$, —C(CH$_3$)$_3$, —C(CH$_3$)$_2$ or p-F-$C_6H_4$ and $R^2$ is —C(CH$_3$)$_3$.

3. A process for preparing the compounds claimed in claim 1 which comprises reducing a diketone of general formula (II):

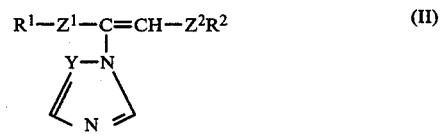

wherein Y, $R^1$ and $R^2$ are as defined, and the groups $Z^1$ and $Z^2$ are C=O, or acid addition salt or copper, zinc, manganese or iron complex thereof, with a reducing agent selected from the group consisting of lithium aluminum hydride, sodium borohydride or aluminum isopropoxide, in an inert polar solvent.

4. A process as claimed in claim 3 wherein the starting materials therefor are made by reacting 1,2,4-triazole, or acid addition salt thereof, with the appropriate dihalo-δ-diketone of general formula (III):

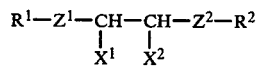 (III)

wherein $R^1$, $R^2$, $Z^1$ and $Z^2$ are as defined, and each of the groups $X^1$ and $X^2$, which may be the same or different, is halogen.

5. A process as claimed in claim 4 wherein the dihalo-δ-diketone starting material is made by halogenation of a compound of general formula (IV):

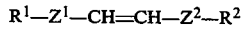 (IV)

wherein $R^1$, $R^2$, $Z^1$ and $Z^2$ are as defined in claim 4 for the compound of general formula (II).

6. A process for preparing the compounds claimed in claim 1 which comprises reacting a compound of general formula (V):

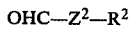 (V)

where Y and $R^1$ are as defined and $Z^1$ is C=O, with a compound of general formula (VI):

OHC—$Z^2$—$R^2$ (VI)

where $R^2$ is as defined and $Z^2$ is C=O, in the presence of a base to give a compound of general formula (VII):

 (VII)

wherein Y, $R^1$ and $R^2$ are as defined above and $Z^1$ and $Z^2$ are C=O, and thereafter subjecting the compound of general formula (VII) to dehydration to give the compound of general formula (II).

7. A composition for combating fungi comprising, as an active ingredient, an effective amount of a compound as claimed in claim 1; together with a carrier or diluent for the active ingredient.

8. A method of combating fungal diseases which comprises applying to a plant, or to seed, or to the locus of a plant or seed, an effective amount of a compound as claimed in claim 1.

* * * * *